United States Patent [19]

Schulz et al.

[11] Patent Number: 5,898,070
[45] Date of Patent: Apr. 27, 1999

[54] PROCESS FOR THE PRODUCTION OF ALKYL AND/OR ALKENYL OLIGOGLYCOSIDES

[75] Inventors: Paul Schulz, deceased, late of Wuppertal, by Brigitte Pflueger-Schulz, heir; Rainer Eskuchen, Langenfeld; Michael Nitsche, Solingen, all of Germany

[73] Assignee: Henkel Corporation, Gulph Mills, Pa.

[21] Appl. No.: 08/793,018

[22] PCT Filed: Aug. 9, 1995

[86] PCT No.: PCT/EP95/03158

§ 371 Date: Mar. 17, 1997

§ 102(e) Date: Mar. 17, 1997

[87] PCT Pub. No.: WO96/05210

PCT Pub. Date: Feb. 22, 1996

[30] Foreign Application Priority Data

Aug. 17, 1994 [DE] Germany .................. 44 29 134

[51] Int. Cl.$^6$ .............. C07G 3/00; C07H 1/00; C07H 15/04
[52] U.S. Cl. .......................... 536/18.6; 536/18.5
[58] Field of Search ................... 536/18.5, 18.6

[56] References Cited

U.S. PATENT DOCUMENTS

| | | | |
|---|---|---|---|
| 4,939,245 | 7/1990 | Rasche et al. | 536/18.6 |
| 5,206,357 | 4/1993 | Schmidt | 536/18.6 |
| 5,212,292 | 5/1993 | Ripke | 536/18.6 |
| 5,374,716 | 12/1994 | Biermann et al. | 536/18.6 |

FOREIGN PATENT DOCUMENTS

| | | |
|---|---|---|
| 0 301 298 | 2/1989 | European Pat. Off. . |
| 0 492 397 | 7/1992 | European Pat. Off. . |
| 0 501 032 | 9/1992 | European Pat. Off. . |
| 0 514 628 | 11/1992 | European Pat. Off. . |
| 42 31 833 | 3/1994 | Germany . |
| 2 132 202 | 7/1984 | United Kingdom . |
| WO 90/03977 | 4/1990 | WIPO . |
| WO 93/11143 | 6/1993 | WIPO . |

OTHER PUBLICATIONS

Skin Care Forum,. (Oct. 1992) p. 1.
Seifen–Öle–Fette–Wachse 118,(1992) p. 894.
Seifen–Öle–Fette–Wachse 118,(1992) p. 905.

*Primary Examiner*—Douglas W. Robinson
*Assistant Examiner*—Everett White
*Attorney, Agent, or Firm*—Ernest G. Szoke; Wayne C. Jaeschke; Henry E. Millson, Jr.

[57] ABSTRACT

The invention relates to an improved process for the production of alkyl and/or alkenyl oligoglycosides corresponding to formula (I):

$$R^1O\text{-}[G]_p \qquad (I)$$

in which $R^1$ is an alkyl and/or alkenyl radical containing 4 to 22 carbon atoms, G is a sugar unit containing 5 or 6 carbon atoms and p is a number of 1 to 10, by acid-catalyzed acetalization of primary alcohols with monomeric carbohydrates, in which the reaction is carried out in a stirred tank reactor surmounted by a vacuum falling-film evaporator through which the mixture is pumped under reaction conditions.

24 Claims, No Drawings

PROCESS FOR THE PRODUCTION OF ALKYL AND/OR ALKENYL OLIGOGLYCOSIDES

This application is a 371 of PCT/EP95/03158, filed Aug. 9, 1995.

BACKGROUND OF THE INVENTION

1. Field of the Invention

This invention relates to a process for the production of alkyl and/or alkenyl oligoglycosides in which a combination of a stirred tank reactor and a falling-film evaporator is used.

2. State of Related Art

Alkyl oligoglycosides, more particularly alkyl oligoglucosides, are nonionic surfactants which are acquiring increasing significance by virtue of their excellent detergent properties and their high ecotoxicological compatibility. The production and use of these compounds have been described just recently in a number of synoptic articles, of which the articles by H. Hensen in Skin Care Forum, 1, (October 1992), D. Balzer and N. Ripke in Seifen-öle-Fette-Wachse 118, 894 (1992) and B. Brancq in Seifen-öle-Fette-Wachse 118, 905 (1992) are cited as representative.

They are normally produced by acetalization of glucose with fatty alcohols in the presence of acidic catalysts. The catalyst is then neutralized, excess fatty alcohol is removed and, if desired, the product is bleached.

There are numerous known processes for their production which are characterized by the use of certain units. For example, DE-A1 4 231 833 (Hüls) describes an acetalization reaction which is carried out as a liquid/liquid reaction in a thin-layer evaporator. Another process for the production of alkyl glucosides, in which the acetalization reaction is carried out in an evaporator at an acid value of 1 to 10, is known from EP-A1 0 501 032 (Hüls). Finally, a process in which aqueous starch sirup is introduced into the reaction solution through an in-line mixer is known from WO 93/11143 (Henkel).

The discontinuous acetalization reaction is normally carried out in stirred reactors which are equipped with a distillation head for removing the water of condensation. Under laboratory conditions, substantially complete conversions can be obtained in short times, in addition to which the reaction products are distinguished by a low polysugar content. However, scaling-up for industrial application involves difficulties. More particularly, it has been found that much longer reaction times are required for complete reaction of the glucose, resulting in an unwanted increase in secondary products, more particularly the polysugar content, quite apart from longer reactor possession times.

Accordingly, the problem addressed by the present invention was to provide an improved process for the production of alkyl glucosides which would be free from the disadvantages mentioned above.

DESCRIPTION OF THE INVENTION

The present invention relates to a process for the production of alkyl and/or alkenyl oligoglycosides corresponding to formula (I):

$$R^1O\text{-}[G]_p \tag{I}$$

in which $R^1$ is an alkyl and/or alkenyl radical containing 4 to 22 carbon atoms, G is a sugar unit containing 5 or 6 carbon atoms and p is a number of 1 to 10, by acid-catalyzed acetalization of primary alcohols with monomeric carbohydrates, in which the reaction is carried out in a stirred tank reactor surmounted by a vacuum falling-film evaporator through which the mixture is pumped under reaction conditions.

It has surprisingly been found that, by comparison with conventional processes, pumping of the reaction mixture through a falling-film evaporator enables equally high conversions of glucose to be obtained in shorter times and the polyglucose content to be reduced to levels which, normally, are only achieved in laboratory processes. The process according to the invention may be carried out discontinuously although it is preferably carried out continuously.

Alkyl and/or Alkenyl Oligoglycosides

Alkyl and alkenyl oligoglycosides are known materials which may be obtained by the relevant methods of preparative organic chemistry. EP-A1 0 301 298 and WO 90/03977 are cited as representative of the extensive literature available on the subject.

The alkyl and/or alkenyl oligoglycosides may be derived from aldoses or ketoses containing 5 or 6 carbon atoms, preferably glucose. Accordingly, the preferred alkyl and/or alkenyl oligoglycosides are alkyl and/or alkenyl oligoglucosides. Powder forms of glucose, for example dextrose monohydrate, are preferably used as starting materials.

The index p in general formula (I) indicates the degree of oligomerization (DP degree), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is generally a broken number. Alkyl and/or alkenyl oligoglycosides with an average degree of oligomerization p of 1.1 to 3.0 are preferably used. Alkyl and/or alkenyl oligoglycosides with a degree of oligomerization below 1.7 and, more particularly, in the range from 1.2 to 1.4 are preferred from the applicational point of view.

The alkyl or alkenyl radical $R^1$ may be derived from primary alcohols containing 4 to 11 and preferably 8 to 10 carbon atoms. Typical examples are butanol, caproic alcohol, caprylic alcohol, capric alcohol and undecyl alcohol and the technical mixtures thereof which are formed, for example, in the hydrogenation of technical fatty acid methyl esters or in the hydrogenation of aldehydes from Roelen's oxo synthesis. Preferred alkyl oligoglucosides are those with a chain length of $C_8$ to $C_{10}$ (DP=1 to 3) which are obtained as the first runnings in the separation of technical $C_{8\text{-}18}$ coconut oil fatty alcohol by distillation and which may contain less than 6% by weight of $C_{12}$ alcohol as an impurity and also alkyl oligoglucosides based on technical $C_{9/11}$ oxoalcohols (DP=1 to 3).

In addition, the alkyl or alkenyl radical $R^1$ may also be derived from primary alcohols containing 12 to 22 carbon atoms and preferably 12 to 16 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and technical mixtures thereof which may be obtained as described above. Alkyl oligoglucosides based on hydrogenated $C_{12/14}$ coconut oil fatty alcohol with a DP of 1 to 3 are preferred.

Acetalization

The acetalization and working up of the reaction products are known per se. To establish the required degree of oligomerization, the alcohols are used in a calculated excess.

The molar ratio of fatty alcohol to sugar is normally 3:1 to 1:8 and is preferably in the range from 4:1 to 5:1.

In addition to sulfuric acid and sulfuric acid semiesters—formed in situ—of the alcohols used, suitable catalysts are above all alkylbenzenesulfonic acid, p-toluenesulfonic acid, sulfosuccinic acid and other short-chain or long-chain aromatic or aliphatic sulfonic acids or derivatives thereof, the catalysts being used in a concentration of 0.1 to 5% by weight and preferably in a concentration of 0.5 to 3% by weight, based on the sum total of the starting materials.

In choosing the acetalization temperature, it is important to bear in mind that glucose decomposes rapidly at temperatures above 120° C. Accordingly, the reaction temperature is preferably in the range from 100 to 110° C. while the pressure is in the range from 5 to 50 mbar. Under these conditions, the water of reaction can be continuously distilled off from the reaction equilibrium and the equilibrium shifted onto the side of the target products.

Falling-Film Evaporators

Falling-film evaporators are evaporators in which evaporation takes place from a thin layer with a thickness of typically 0.1 to 10 mm. In the most simple form, the liquid is distributed by trickling down. A particular form of falling-film evaporators are thin-layer evaporators in which the liquid is distributed by centrifugal forces or by rotating fittings, for example wipers. The residence time of the products in the heated evaporator zone is typically between 0.1 and 30 s. Falling-film evaporators which have an exchange surface of 1 to 30 and preferably 15 to 25 m$^2$/t reaction mixture are preferably used in the process according to the invention. The pumping rate is advantageously 1 to 20 and preferably 5 to 15 t/h/t reaction mixture. The combination of a reactor and thin-layer evaporator is particularly suitable for continuously carrying out glucosidation reactions, for example in cascades of 2 to 4 reactors.

Commercial Applications

The alkyl and/or alkenyl oligoglycosides obtainable by the process according to the invention are distinguished by an advantageously low polysugar content and are suitable for the production of laundry detergents, dishwashing detergents and cleaning products and also hair-care and personal hygiene products, in which they may be present in quantities of 1 to 50% by weight and preferably in quantities of 5 to 25% by weight, based on the particular product.

The following Examples are intended to illustrate a the invention without limiting it in any way.

EXAMPLES

Comparison Examples C1 to C3

Dextrose monohydrate and $C_{12/14}$ coconut oil fatty alcohol (LOROLO®S, a product of Henkel KGaA, Dusseldorf, FRG) in a molar ratio of 1:5 were introduced into a stirred tank reactor equipped with a distillation head, followed by the addition of 2% by weight of dodecylbenzenesulfonic acid as catalyst. The mixture was heated with stirring to 105° C. under a reduced pressure of 30 mbar, the water of condensation distilling off continuously. After all the water had been removed, the vacuum was broken and the mixture was cooled. The new catalyst was neutralized by addition of magnesium oxide and sodium hydroxide solution and the excess fatty alcohol was removed in known manner in a two-stage distillation assembly using a falling-film evaporator and a thin-layer evaporator. The results are set out in Table 1.

Example 1

The procedure was as in Comparison Example 2, except that the combination of the stirred tank reactor and the distillation head was replaced by a stirred tank reactor surmounted by a falling-film evaporator with an exchange surface of 20 m$^2$ through which the suspension was pumped at a rate of 20 t/h (corresponding to 10 t/h/t reaction mixture). Working up was carried out as described above. The results are again set out in Table 1.

TABLE 1

| | Characteristic data of the tests | | |
|---|---|---|---|
| Ex. | Batch size kg | Reaction time h | Polyglucoside content % by weight |
| C1 | 2 | 4.5 | 2.5 |
| C2 | 2,000 | 5.5 | 5.0 |
| C3 | 20,000 | 6.5 | 6.0 |
| 1 | 2,000 | 4.5 | 2.7 |

The expression "batch size" as used in Table 1 is understood to be the sum total of the starting materials fatty alcohol+glucose.

It can be seen that, in terms of reaction time and polyglucose content, the process according to the invention gives results which could otherwise only be achieved under laboratory conditions.

We claim:

1. A process for the production of alkyl and/or alkenyl oligoglycosides corresponding to formula (I):

$$R^1O\text{-}(G)_p \quad \text{(I)}$$

in which R$^1$ is an alkyl and/or alkenyl radical containing 8 to 22 carbon atoms, G is a sugar unit containing 5 or 6 carbon atoms and p is a number of 1 to 10, comprising the steps of A) adding to a stirred tank reactor surmounted by a vacuum falling-film evaporator
 a) at least one alcohol containing from 8 to 22 carbon atoms,
 b) at least one monomeric sugar containing 5 or 6 carbon atoms, and
 c) an acidic catalyst, to form a reaction mixture; and B) heating the reaction mixture to reaction temperature and pumping the reaction mixture through the falling-film evaporator at the reaction temperature.

2. The process of claim 1 wherein in step A) component a) is at least one primary alcohol containing from 8 to 10 carbon atoms.

3. The process of claim 1 wherein in step A) component a) is at least one primary alcohol containing from 12 to 22 carbon atoms.

4. The process of claim 3 wherein the at least one alcohol contains from 12 to 16 carbon atoms.

5. The process of claim 1 wherein in step A) component a) is technical $C_{9/11}$ oxoalcohol.

6. The process of claim 1 wherein in step A) component a) is hydrogenated $C_{12/14}$ coconut oil fatty alcohol.

7. The process of claim 1 wherein in step A) component b) is a glucose.

8. The process of claim 7 wherein the glucose is dextrose monohydrate.

9. The process of claim 1 wherein in formula I, p=1 to 6.

10. The process of claim 9 wherein p=1.1 to 3.0.

11. The process of claim 10 wherein p=1.2 to 1.4.

12. The process of claim 1 wherein in step A) components a) and b) are present in a molar ratio of a): b) of from about 3:1 to about 8:1.

13. The process of claim 12 wherein the molar ratio is from about 4:1 to about 5:1.

14. The process of claim 1 wherein in step A) component c) is alkylbenzenesulfonic acid, p-toluenesulfonic acid, or sulfosuccinic acid.

15. The process of claim 14 wherein component c) is present in from about 0.1 to about 5% based on the sum of components a) through c).

16. The process of claim 1 wherein the falling-film evaporator has an exchange surface of from about 1 to about 30 $m^2/t$ reaction mixture.

17. The process of claim 16 wherein the exchange surface is from about 15 to about 25 $m^2/t$.

18. The process of claim 1 wherein in step B) the pumping rate is from about 1 to about 20 t/h/t reaction mixture.

19. The process of claim 18 wherein the pumping rate is from about 5 to about 15 t/h/t.

20. The process of claim 1 wherein in step B) the reaction temperature is in the range of from about 100 to about 110° C., and the reaction pressure is in the range of from about 5 to about 50 mbar.

21. The process of claim 1 wherein in step A) component a) is a primary alcohol or an oxoalcohol, and component b) is a glucose.

22. The process of claim 21 wherein in formula I, p=1 to 6, and in step A) components a) and b) are present in a molar ratio of a): b) of from about 3:1 to about 8:1.

23. The process of claim 22 wherein in step A) component c) is alkylbenzenesulfonic acid, p-toluenesulfonic acid or sulfosuccinic acid, and component c) is present in from about 0.1 to about 5% based on the sum of components a) through c).

24. The process of claim 22 wherein in step B) the reaction temperature is in the range of from about 100 to about 110° C., and the reaction pressure is in the range of from about 5 to about 50 mbar;

the falling-film evaporator has an exchange surface of from about 1 to about 30 $m^2/t$ reaction mixture; and in step B) the pumping rate is from about 1 to about 20 t/h/t reaction mixture.

* * * * *